United States Patent [19]

Yeakel et al.

[11] Patent Number: 5,042,261
[45] Date of Patent: Aug. 27, 1991

[54] TISSUE FREEZING PROCESS

[75] Inventors: James D. Yeakel; John H. Cornwell, both of Kinnelon, N.J.

[73] Assignee: Cornwell Corporation, Riverdale, N.J.

[21] Appl. No.: 472,318

[22] Filed: Jan. 30, 1990

[51] Int. Cl.⁵ .............................................. F25D 17/02
[52] U.S. Cl. .......................................... 62/64; 62/293; 62/320
[58] Field of Search ............................ 62/64, 293, 320

[56] References Cited

U.S. PATENT DOCUMENTS

| 3,820,352 | 6/1974 | Mahler | 62/293 |
| 3,830,239 | 8/1974 | Stumpf et al. | 62/293 |
| 3,901,241 | 8/1975 | Allen, Jr. | 62/293 |

Primary Examiner—Ronald C. Caposse
Attorney, Agent, or Firm—Ribis, Graham & Curtin

[57] ABSTRACT

A histological tissue freezing process is provided. The process includes an aerosol can with an adjustable flow rate spray unit for spraying a chemical, monochlorodifluoromethane, onto a portion of a histological tissue specimen before sectioning thereof. The use of monochlorodifluoromethane has the dual advantage reducing ozone depletion and producing a colder spray. The spray means has a horizontal hinged spray bar with a passage with a spray outlet and has a horizontal hinged actuator plate with a trigger for slightly turning the actuator plate unit and spray bar. A tube has a passage connecting to the spray bar passage. The tube has an upper end coupled to the spray bar and an intermediate end extending through a can upper wall and a lower end disposed inside the can. The tube lower end has an adjustable orifice opening. The tube also has a latching unit, a compression spring, and seal ring.

4 Claims, 1 Drawing Sheet

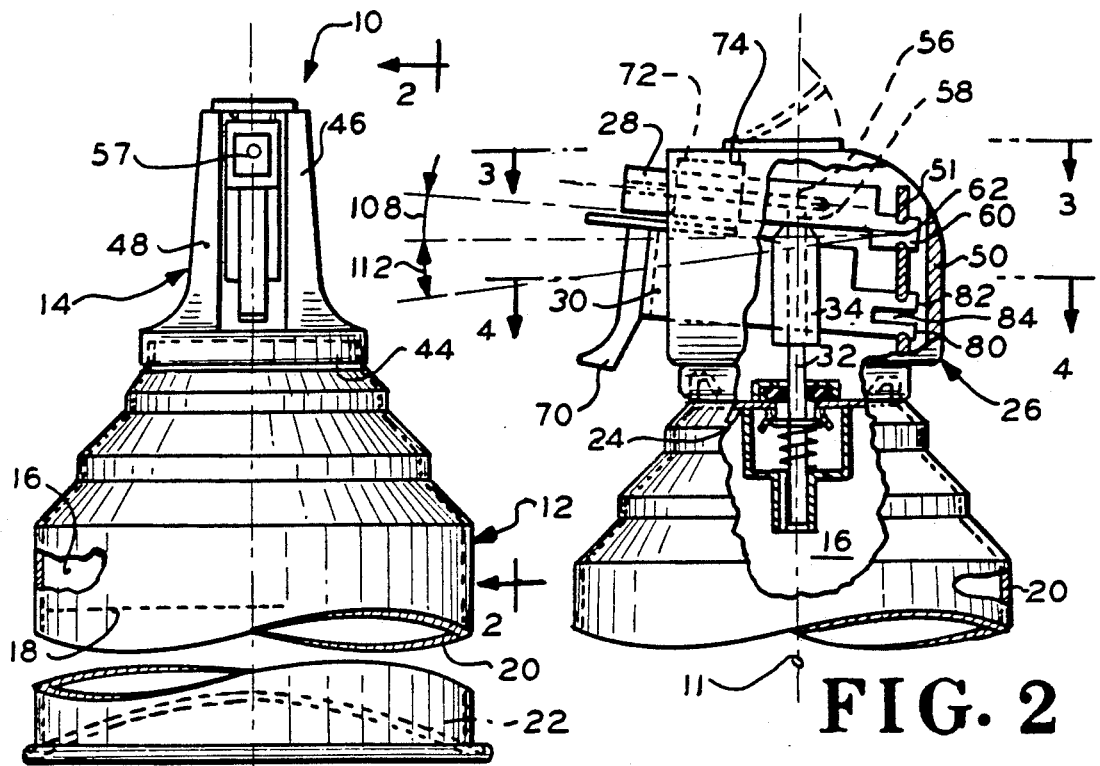

TISSUE FREEZING PROCESS

The invention relates to a histological tissue freezing process, and in particular the invention relates to a tissue freezing process which has limited environmental effects and utilizes a special valve.

BACKGROUND OF THE INVENTION

The prior art histological tissue freezing apparatus includes a container enclosing a cavity having a selective pressurized fluid such as dichlorodifluoromethane, and a spray means having a non-adjustable flow valve with a button actuator.

One problem with the prior art tissue freezing apparatus is that it causes release of gases which are detrimental to the atmosphere. A further disadvantage is that during successive tissue freezing, and cuttings with a special knife, of tissue specimens, finger fatigue occurs. A still further disadvantage is that it is necessary to stop spraying to change flow rate.

SUMMARY OF THE INVENTION

According to the present invention, a histological tissue freezing process is provided. This process utilizes a container enclosing a cavity having as the selective pressurized fluid monochlorodifluoromethane, and a spray means having a trigger actuator and an adjustable flow control.

The use of monochlorodifluoromethane prevents ozone depletion as is a major advantage of the invention. Also by using a trigger actuator, finger fatigue is minimized. Also, by using an adjustable flow control, spray flow rate is better controlled to suit each tissue specimen The foregoing and other objects, features and the advantages of the invention will be apparent from the following description of the preferred embodiment of the invention as illustrated in the accompanying drawings.

BRIEF DESCRIPTION OF THE DRAWINGS

FIG. 1 is an elevation view of a histological tissue freezing apparatus according to the invention;

FIG. 2 is a partially cutaway elevation view as taken along the line 2—2 of FIG. 1;

FIG. 3 is a section view as taken along the line 3—3 of FIG. 2;

FIG. 4 is a section view as taken along the line 4—4 of FIG. 2;

FIG. 5 is an enlarged view of a portion of FIG. 2; and

FIG. 6 is a partial elevation view as taken along the line 6—6 of FIG. 5.

DESCRIPTION OF THE PREFERRED EMBODIMENT

As shown in FIG. 1, a tissue freezing apparatus 10 is provided. Apparatus 10, which has an axis 11, includes a container or can 12 and a spray means 14. Container 12 encloses a cavity 14 which contains fluid monochlorodifluoromethane 18 under pressure. The fluid 18 is sprayed as a gaseous composition by spray means 14 onto a histological tissue specimen, prior to sectioning or cutting a difficult tissue specimen such as fatty tissue or frozen tissue. The sectioning is done by a microtome or a special knife which cuts sections down to 1 to 2 microns thickness. The freezing aerosol is used to flash freeze the specimen to keep it hard while sectioning. That procedure prevents the microtome from compressing or tearing the specimen being sectioned which destroys the cellular detail that is examined microscopically.

Can 12 is preferably filled to about 12 ounces. Can 12 in this embodiment is about 2.50 inches in outside diameter and is about 6.75 inches in height. Spray means or nozzle 14 is an integral trigger type nozzle which has an adjustable flow rate that is controlled by finger pressure. Fluid or chemical 18 in this embodiment is monochloridifluoromethane.

As shown in FIGS. 1 and 2, can 12 includes a peripheral wall 20, a bottom wall 22, and a top wall 24. Walls 20, 22, 24 enclose cavity 16.

As shown in FIGS. 1, 2, 3, 4, and 5, spray means 14 includes a support 26, a spray bar 28, and an actuator 30. Spray means 14 also includes a tube 32 which has a positioning collar 34. Spray means 14 also includes a seal ring 36 as shown in FIG. 5, a latch unit 38, a compression spring 40, and an adjustable flow control 42.

Support 26 has an annular base 44, a near wall 46, a far wall 48, and an end wall 50. Support 26 also has a portion wall 51, which has an upper slot 52 for spray bar 28, and which has two respective near and far slots 53, 54 for actuator 30.

As shown in FIGS. 1, 2 and 3, spray bar 28 has a horizontal passage 56, a vertical passage 58 which connects to horizontal passage 56, and a hinge extension 60 which has a hinge axis 62, Bar 28 has an outlet 57 from passage 56.

As shown in FIGS. 1, 2 and 4, actuator 30 has a rear plate 64, a far plate 66, and an end plate or wall 68, which has a trigger portion 70. Actuator 30 also has a U-shaped strap or plate 72. Strap 72, which is a locking strap for shipment and for making apparatus 10 tamperproof. Strap 72 has a flexible strip 74 and has two tie members 76, 78. Tie members 76, 78 are broken by peeling back strip 74 just prior to unlocking and using spray 14, as shown in FIG. 2. Actuator plates 65, 66 have respective hinge extensions 80, 82 which have a common hinge axis 84.

As shown in FIG. 5, tube 32 has a washer or projection 86, which is fixedly connected thereto. Tube 32 also has an inner passage 88, which connects to spray bar passage 58. Tube 32 has a cylindrical wall 90 and a closed end wall 92. Seal ring 36 has a holder ring 94, which has an L-shaped cross-section, and which is fixedly connected to top wall 24. Seal ring 36 minimizes leakage of fluid 18 from cavity 16.

Latch unit 38 has a spider ring 96, which is fixedly connected to top wall 24. Spider ring 96 has a plurality of spider legs 98 for gripping washer 86 in an upward or latched position. Spring 40 has a cup-shaped ring 100, which has a tubular portion 102. Adjustable control 42 has a V-shaped opening or orifice 104.

In operation, finger pressure by a user onto trigger 70 slightly rotates actuator plates 64, 66 about actuator axis 84. Such rotation of plates 64, 66 causes spray bar 28 to slightly rotate about bar axis 62. Such rotation of bar 28 causes tube 32 to move vertically. Downward movement of trigger 70 causes downward movement of tube 32 which releases washer 86 from spider ring 96. As shown in FIGS. 2 and 6, during downward movement of trigger 70, tube 32 moves through an unlatch distance 106 while bar 28 moves through an unlatch angle 108; and tube 32 moves through a spray condition distance 110 while bar 28 moves through a spray condition angle 112. The spray means can have a conventional extender such as a hollow tube.

The process includes, positioning a tissue specimen prior to sectioning thereof, applying a spray of a chemical, monochlorodifluoromethane, to a selected portion of the tissue specimen; adjusting a flow rate of the spray according to the type of specimen while freezing the specimen; and applying a force from the inner surface of a users pointer finger to adjust the flow rate.

The advantages of the process are indicated hereafter
A) Ozone depletion potential is reduced.
B) Apparatus 10, which in this embodiment has a fluid 18 of a relatively low boiling point of about minus 40.8 Fahrenheit, provides a relatively colder spray, as compared to the prior art apparatus, thereby providing faster freezing and reduced wastage.
C) Flow rate is more easily controlled while freezing a specimen so that specimen damage is minimized.
D) Finger fatigue is more easily reduced because can 12 is easily gripped by a user while applying finger pressure on trigger 70.

The process includes, positioning a tissue specimen prior to sectioning thereof, applying a spray of a chemical, monochlorodifluoromethane, to a selected portion of the tissue specimen; adjusting a flow rate of the spray according to the type of specimen while freezing the specimen; and applying a force from the inner surface of a users pointer finger to adjust the flow rate.

While the invention has been described in its preferred embodiment, it is to be understood that the words which have been used are words of description rather than limitation and that changes may be made within the purview of the appended claims without departing from the true scope and spirit of the invention in its broader aspects.

What is claimed is:

1. A process for freezing at least a portion of a tissue specimen prior to cutting thin sections from the specimen using a tissue freezing apparatus comprising a can having walls enclosing a cavity and having upper and lower end walls, said cavity containing monochlorodifluromethane as a liquid freezing agent; a spray bar having first passage means with a spray outlet and having a hinge with a hinge axis; an actuator plate coupled to the spray bar and having a trigger for slightly rotating the actuator plate and spray bar; a tube having second passage means connecting to the first passage means and having a first end portion coupled to the spray bar and having an intermediate portion extending through a can wall and having a second end portion disposed in said cavity; and flow control means for varying the flow of the fluid and having an orifice portion mounted on the tube second end portion and having a tubular portion mounted on a can upper end wall for adjusting a fluid flow which is adjusted by a position of the orifice portion which is adjusted by a travel distance of the tube which is adjusted by a travel angle of the spray bar and actuator plate; and including the steps of positioning the tissue specimen to allow cutting of thin sections; applying a spray of the liquid freezing agent to a selected portion of the tissue specimen to the selected section; adjusting the application according to the condition and characteristics of the tissue specimen to freeze the selected portion of the specimen and cutting thin sections from the selected portion of the specimen.

2. A tissue freezing apparatus comprising: a can having walls enclosing a cavity and having upper and lower end walls, said cavity containing monochlorodifluromethane as a liquid freezing agent; a spray bar having first passage means with a spray outlet and having a hinge with a hinge axis; an actuator plate coupled to the spray bar and having a hinge with a hinge axis and having a trigger for slightly rotating the actuator plate and spray bar; a tube having second passage means connecting to the first passage means and having a first end portion coupled to the spray bar and having an intermediate portion extending through a can wall and having a second end portion disposed in said cavity; and flow control means for varying the flow of the fluid and having an orifice portion mounted on the tube second end portion and having a tubular portion mounted on a can upper end wall for adjusting a fluid flow which is adjusted by a position of the orifice portion which is adjusted by a travel distance of the tube which is adjusted by a travel angle of the spray bar and actuator plate.

3. The apparatus as defined in claim 2, including: seal means mounted on the can upper end wall and engaging the tube intermediate portion for minimizing fluid leakage from the cavity; latch means mounted on the can upper end wall for gripping the tube in a latched position and for releasing the tube in an unlatched position; and spring means for urging the tube toward its latched position;

4. The apparatus as defined in claim 2, including: support means having an annular position mounted on the can upper end wall having a pair of spaced sidewalls mounted on the annular portion and having a partition wall supported by the pair of sidewalls and supporting the spray bar hinge and the actuator plate hinge; and tamper-proofing lock means including a flexible lock strip having a pair of breakable tie members fixedly connected to a strap portion of the actuator plate.

* * * * *